United States Patent [19]
Wu et al.

[11] Patent Number: 5,877,379
[45] Date of Patent: Mar. 2, 1999

[54] OLEFIN CONVERSION PROCESS INVOLVING COKE SUPPRESSOR IMPREGNATED CATALYST

[75] Inventors: An-hsiang Wu; Charles A. Drake, both of Bartlesville, Okla.

[73] Assignee: Phillips Petroleum Company, Bartlesville, Okla.

[21] Appl. No.: 700,243

[22] Filed: Aug. 19, 1996

[51] Int. Cl.$^6$ .................................................. C07C 6/00
[52] U.S. Cl. .................... 585/643; 585/646; 585/664; 585/666; 585/667; 585/668; 585/661; 208/134
[58] Field of Search ................................ 585/643, 646, 585/664, 666, 667, 668, 661; 208/134

[56] References Cited

U.S. PATENT DOCUMENTS

| | | | |
|---|---|---|---|
| 3,933,974 | 1/1976 | Winquist | 423/118 |
| 4,000,248 | 12/1976 | Martin | 423/329 |
| 4,343,692 | 8/1982 | Winquiest | 208/111 |
| 4,436,949 | 3/1984 | Myers et al. | 585/664 |
| 4,663,025 | 5/1987 | Chia-Min | 208/120 |
| 4,749,819 | 6/1988 | Hamilton, Jr. | 585/329 |
| 4,975,399 | 12/1990 | Gardner | 502/38 |
| 4,996,386 | 2/1991 | Hmilton, Jr. et al. | 585/646 |
| 5,043,520 | 8/1991 | Hamilton, Jr. et al. | 585/646 |
| 5,516,956 | 5/1996 | Abichandani et al. | 585/481 |
| 5,633,422 | 5/1997 | Murray | 585/666 |

OTHER PUBLICATIONS

Kirk–Othmer Encycl. Chem. Technol. 3rd ed., vol. 20, p0p. 962–973 (John Wiley & Sons, New Yorks, 1980) No month.

*Primary Examiner*—Walter D. Griffin
*Assistant Examiner*—Nadine Preisch
*Attorney, Agent, or Firm*—Lucas K. Shay

[57] ABSTRACT

A composition and an olefin conversion process are disclosed. The composition comprises a zeolite having incorporated therein a coke-suppressing amount of a coke suppressor selected from the group consisting of silicon oxides, phosphorus oxides, boron oxides, magnesium oxides, tin oxides, titanium oxides, zirconium oxides, molybdenum oxides, germanium oxides, indium oxides, lanthanum oxides, cesium oxides, and combinations of any two or more thereof. The olefin conversion process comprises contacting a first olefin with a catalyst composition under a condition effective to convert said first olefin to a second olefin wherein the catalyst composition is the same as the composition disclosed above. Also disclosed is a process for producing the composition.

16 Claims, No Drawings

OLEFIN CONVERSION PROCESS INVOLVING COKE SUPPRESSOR IMPREGNATED CATALYST

FIELD OF THE INVENTION

The present invention relates to a composition and a process for conversion of an olefin.

BACKGROUND OF THE INVENTION

The conversion of an olefin into another olefin is well known to one skilled in the art. For example, U.S. Pat. No. 4,436,949 discloses a process for olefin conversions in which water is added to an olefin to form a water-containing olefin followed by contacting the water-containing olefin with an acidic alumina. In addition to an alumina, a ferrierite has also been employed as catalyst for olefin conversions. See, for example, U.S. Pat. No. 5,510,560.

One of the problems facing the industry is the formation of coke which is a semi-pure carbon during olefin conversions. In order to burn out the deposits of coke, an olefin conversion reactor is periodically shut down resulting in a substantial loss of production of olefin conversion product. Additionally, coke is a poor heat conductor as coke is deposited. Consequently, a higher temperature is required to maintain the desired reactor temperature thereby increasing fuel consumption and giving shorter reactor life. Additionally, the known olefin conversion processes generally produce abundance of lower valued heavies and lights.

Another problem is that the coke formed can deposit on the surface of a catalyst thereby resulting in decreased catalystic stability and activity.

A further problem facing the industry is that, during an olefin conversion process, a appreciable quantity of undesirable by-products are also produced. Undesirable by-products decrease the efficiency of an olefin conversion process.

Therefore, there is ever-increasing need for developing a process which has higher olefin conversion than that which has been achieved in the art because certain olefin conversion products can have important commercial and industrial applications. For example, isobutene which can be produced from the disproportionation of propylene or isomerization of n-butene can be further reacted with methanol to form methyl tertiary butyl ether (MTBE) which is an important and useful additive in gasoline as an octane improver. There is also a need to develop a composition that can be used for olefin conversion with reduced coke formation during the conversion process.

SUMMARY OF THE INVENTION

An object of the present invention is to provide a catalyst composition that can be used for olefin conversion. Another object of the present invention is to provide a process for producing the catalyst composition. A further object of the present invention is to provide a process for olefin conversion using the catalyst composition. An advantage of the present invention is that the present invention olefin conversion process decreases coke deposits and lowers the formation of heavies and lights. Other objects and advantages will become more apparent as the invention is more fully disclosed hereinbelow.

According to a first embodiment of the invention, a composition which can be used as catalyst in olefin conversions is provided. The composition comprises a zeolite having incorporated therein a coke suppressor selected from the group consisting of silicon oxides, phosphorus oxides, boron oxides, magnesium oxides, tin oxides, titanium oxides, zirconium oxides, molybdenum oxides, germanium oxides, indium oxides, lanthanum oxides, cesium oxides, and combinations of any two or more thereof wherein said coke suppressor is present in said composition in a coke-suppressing amount to suppress coke formation when said composition is used in an olefin conversion process.

According to a second embodiment of the invention, a process for producing a composition which can be used as catalyst in olefin conversions is provided. The process comprises (1) contacting a zeolite with a coke suppressor precursor selected from the group consisting of silicon-containing compounds, phosphorus-containing compound, boron-containing compounds, magnesium-containing compounds, tin-containing compounds, titanium-containing compounds, zirconium-containing compounds, molybdenum-containing compounds, germanium-containing compounds, indium-containing compounds, lanthanum-containing compounds, cesium-containing compounds, and combinations of any two or more thereof under a condition sufficient to incorporate the coke suppressor onto the zeolite to form a modified zeolite; and (2) calcining the modified zeolite under a condition sufficient to convert the coke suppressor precursor to its oxide form wherein the amount of the coke suppressor precursor is the amount that is sufficient to suppress coke formation when said composition is used in an olefin conversion process.

According to a third embodiment of the invention, an olefin conversion process which can be used for disproportionation or isomerization of olefins is provided. The process comprises contacting an olefin with a catalyst composition, optionally in the presence of hydrogen, under a condition effective to convert the olefin to another olefin which is different from the olefin being contacted with the catalyst, wherein the composition is the same as that disclosed in the first embodiment of the invention.

DETAILED DESCRIPTION OF THE INVENTION

As used in the invention, the term "olefin conversion" includes olefin disproportionations, olefin isomerizations, and combinations thereof.

According to the first embodiment of the invention, a composition comprising, consisting essentially of, or consisting of a zeolite having impregnated thereon a coke suppressor is provided. The weight ratio of the coke suppressor to zeolite can be any ratio so long as the ratio can suppress or reduce the formation of coke on a zeolite-based catalyst during conversion of an olefin. Generally, the ratio can be in the range of from about 0.0001:1 to about 1:1, preferably about 0.0005:1 to about 1:1, more preferably about 0.001:1 to about 0.8:1 and most preferably from 0.005:1 to 0.5:1 for an effective olefin conversion and coke reduction or suppression. Alternatively, the coke suppressor can be present in the catalyst composition in the range of from about 0.01 to about 50, preferably about 0.05 to about 50, more preferably about 0.1 to about 45, and most preferably 0.5 to 33 grams per 100 grams of the catalyst composition.

Any zeolite which is known to one skilled in the art to be capable of catalyzing olefin conversion can be employed in the present invention. It is presently preferred that a ferrierite generally prepared as ammonium or alkali metal aluminosilicate be used. A ferrierite may also be converted to acid form by calcination or by treatment with, for example, aqueous ammonium nitrate, ammonium chloride followed by calcination. A synthetic ferrierite can be prepared by any methods known to one skilled in the art such as those disclosed in U.S. Pat. Nos. 3,933,974; 4,000,248; and 4,343,692, disclosures of which are incorporated herein by reference.

According to the present invention, any coke suppressor that, as compared to use of zeolite only, can effect the reduction of coke deposit on an olefin conversion catalyst during conversion of an olefin to a more desired olefin can be employed. Presently it is preferred that the coke suppressor is selected from the group consisting of silicon oxides, phosphorus oxides, boron oxides magnesium oxides, tin oxides, titanium oxides, zirconium oxides, molybdenum oxides, germanium oxides, indium oxides, lanthanum oxides, cesium oxides, and combinations of any two or more thereof.

Any methods known to one skilled in the art for incorporating a compound or a portion thereof into a zeolite such as, for example, impregnation or extrusion can be employed for producing the composition of the present invention. However, it is presently preferred the composition be produced by the process disclosed in the second embodiment of the invention.

According to the second embodiment of the invention, a zeolite, preferably a ferrierite, is first contacted with one or more suitable binder in a liquid, preferably aqueous medium to form a zeolite-binder mixture. Any binders known to one skilled in the art for use with a zeolite are suitable for use herein. Examples of suitable binder include, but are not limited to, clays such as for example, kaolinite, halloysite, vermiculite, chlorite, attapulgite, smectite, montmorillonite, illite, saconite, sepiolite, palygorskite, Fuller's earth, and combinations of any two or more thereof; aluminas such as for example $\alpha$-alumina and $\gamma$-alumina; silicas; alumina-silica; aluminum phosphate; aluminum chlorohyrate; and combinations of any two or more thereof. Because these binders are well known to one skilled in the art, description of which is omitted herein. The weight ratio of a zeolite to a binder can be in a wide range and generally in the range of from about 200:1 to about 0.1: 1, preferably 100:1 to 0.01:1.

After the zeolite and the binder are well mixed by any means known to one skilled in the art such as stirring, blending, kneading, or extrusion, the zeolite-binder mixture can then be dried in air at a temperature in the range of from about 50° to about 200° C., preferably about 75° to about 175° C., and most preferably 100° to 150° C. for about 0.5 to about 15 hours, preferably about 1 to about 10 hours, and most preferably 1 to 5 hours, preferably under atmospheric pressure. Thereafter, the dried, zeolite-binder mixture can be calcined in air at a temperature in the range of from about 300° to 1000° C., preferably about 350° to about 750° C., and most preferably 450° to 650° C. to prepare a calcined zeolite-binder.

The calcined zeolite-binder can be treated with a compound containing an exchangeable ammonium ion to prepare an ammonium-exchanged zeolite. Examples of suitable ammonium-containing compound include, but are not limited to, ammonium sulfate, ammonium chloride, ammonium nitrate, ammonium bromide, ammonium fluoride, and combinations of any two or more thereof. Treatment of the zeolite replaces the original ions such as, for example, alkali or alkaline earth metal ions of the zeolite to predominantly ammonium ions. Techniques for such treatment are well known to one skilled in the art such as, for example, ion exchange with the original ions. For example, a zeolite can be contacted with a solution containing a salt of the desired replacing ion or ions.

Generally, the zeolite-binder can be suspended in an aqueous solution of an ammonium-containing compound. The concentration of the zeolite-binder in the aqueous solution can be in the range of from about 0.01 to about 200, preferably about 0.1 to about 150, more preferably about 1 to about 100, and most preferably 5 to 75 grams per liter. The amount of the ammonium-containing compound required is the amount of the original ion(s) to be exchanged. Upon the preparation of the solution, the solution can be subject to a temperature in the range of from about 30° C. to about 200° C., preferably about 40° C. to about 150° C., and most preferably 50° C. to 100° C. for about 1 to about 150 hours, preferably about 5 to about 100 hours, and most preferably 10 to 75 hours depending on desired degrees of ion exchange. The treatment can be carried out under a pressure in the range of from about 1 to about 10 atmospheres (atm), preferably about 1 atm. Thereafter, the treated zeolite-binder can be washed with a running water for 1 to about 60 minutes followed by drying and calcining to produce calcined zeolite. The drying and calcining processes can be carried out substantially the same as those disclosed above for the preparation of a calcined zeolite-binder.

Generally, the ammonium exchanged zeolite becomes hydrogen exchanged upon calcination such that a predominant proportion of its exchangeable cations are hydrogen ions. The above-described ion exchanges of exchangeable ions in a zeolite is well known to one skilled in the art. See, for example, U.S. Pat. No. 5,516,956, disclosure of which is incorporated herein by reference. Because the ion exchange procedure is well known, the description of which is omitted herein for the interest of brevity.

In the next step, the calcined zeolite-binder is impregnated with a coke suppressor precursor. According to the present invention, any coke suppressor precursor which can be converted to a coke suppressor, as disclosed in the first embodiment of the invention, that, as compared to use of zeolite only, can effect the reduction of coke during conversion of an olefin to a more desired olefin can be employed. Presently it is preferred that the coke suppressor precursor is selected from the group consisting of phosphorus-containing compounds, boron-containing compounds, magnesium-containing compounds, tin-containing compounds, titanium-containing compounds, zirconium-containing compounds, molybdenum-containing compounds, germanium-containing compounds, indium-containing compounds, lanthanum-containing compounds, cesium-containing compounds, and combinations of any two or more thereof.

Generally any silicon-containing compounds which can be converted to a silicon oxide that is effective to enhance olefin conversion when used with a zeolite can be used in the present invention. Examples of suitable silicon-containing compounds can have a formula of $(R)(R)(R)Si\text{-}(O_mSi(R)(R))_nR$ wherein each R can be the same or different and is independently selected from the group consisting of hydrogen, alkyl radicals, alkenyl radicals, aryl radicals, alkaryl radicals, aralkyl radicals, and combinations of any two or more thereof; m is 0 or 1; and n is 1 to about 10 wherein each radical can contain 1 to about 15, preferably 1 to about 10 carbon atoms per radical. Specific examples of such polymers include, but are not limited to, silicon-containing polymers such as poly(phenylmethylsiloxane), poly(phenylethylsiloxane), poly(phenylpropylsiloxane), hexamethyldisiloxane, decamethyltetrasiloxane, diphenyltetramethyldisiloxane, and combinations of any two or more thereof. Other silicon-containing compounds include organosilicates such as, for example, tetraethyl orthosilicate. A number of well known silylating agents such as trimethylchlorosilane, chloromethyldimethylchlorosilane, N-trimethylsilylimidazole, N,O-bis(trimethylsilyl) acetimide, N-methyl-N-trimethylsilyltrifluoroacetamie, t-butyldimethylsilylimidazole, N-trimethylsilylacetamide, methyltrimethoxysilane, vinyltriethoxysilane, ethyltrimethoxysilane, propyltrimethoxysilane, (3,3,3-trifluoropropyl)trimethoxysilane, [3-(2-aminoethyl) aminopropyl]trimethoxysilane, cyanoethyltrimethoxysilane, aminopropyltriethoxysilane, phenyltrimethoxysilen, (3-chloropropyl)trimethoxysilane, (3-mercaptopropyl) trimethoxysilane, (3-glycidoxypropyl)trimethoxysilane, vinyltris($\beta$-methoxyethoxy)silane, ($\gamma$-methacryloxypropyl) trimethoxysilane, vinylbenzyl cationic silane, (4-aminopropyl)triethoxysilane, [$\gamma$-($\beta$-aminoethylamino) propyl]trimethoxysilane, ($\gamma$-glycidoxypropyl) trimethoxysilane, [$\beta$-(3,4-epoxycyclohexyl)ethyl] trimethoxysilane, ($\gamma$-mercaptoethyl)trimethoxysilane, ($\gamma$-chloropropyl)trimethoxysilane, and combinations of any two or more thereof can also be employed. The presently preferred silicon-containing compounds are tetraethyl orthosilicate and poly(phenylmethyl) siloxane.

Similarly, any phosphorus-containing compounds that, when impregnated onto a zeolite can be converted into a phosphorus oxide, are capable of enhancing olefin conversion, as compared to the use of the ferrierite only, can be used in the present invention. Examples of suitable phosphorus-containing compounds include, but are not limited to, phosphorus pentoxide, phosphorus oxychloride, phosphoric acid, phosphines having the formula of $P(OR)_3$, $P(O)(OR)_3$, $P(O)(R)(R)(R)$, $P(R)(R)(R)$, and combinations of any two or more thereof wherein R is the same as that disclosed above.

According to the present invention, any boron-containing compound which, upon being incorporated into a zeolite can be converted into a boron oxide can be used in the present invention. Examples of suitable boron-containing compounds include, but are not limited to boric acid, borane-ammonium complex, boron trichloride, boron phosphate, boron nitride, triethyl borane, trimethyl borane, tripropyl borane, trimethyl borate, triethyl borate, tripropyl borate, trimethyl boroxine, triethyl boroxine, tripropyl boroxine, and combinations of any two or more thereof.

Examples of suitable magnesium-containing compounds include, but are not limited to, magnesium formate, magnesium acetate, magnesium bromide, magnesium bromide diethyl etherate, magnesium chloride, magnesium fluoride, magnesium nitrate, magnesium sulfate, dibutyl magnesium, magnesium methoxide, and combinations of any two or more thereof.

Similarly, examples of suitable tin-containing compound include, but are not limited to, stannous acetate, stannic acetate, stannous bromide, stannic bromide, stannous chloride, stannic chloride, stannous oxalate, stannous sulfate, stannic sulfate, stannous sulfide, and combinations of any two or more thereof.

Examples of suitable titanium-containing compounds include, but are not limited to, titanium zinc titanate, lanthanum titanate, titanium tetramides, titanium tetramercaptides, titanium tetrabutoxide, titanium tetramethoxides, titanium tetraethoxide, titanium tetrapropoxide, titanium tetrachloride, titanium trichloride, titanium bromides, and combinations f any two or more thereof.

Similarly, examples of suitable zirconium-containing compounds include, but are not limited to, zirconium acetate, zirconium formate, zirconium chloride, zirconium bromide, zirconium butoxide, zirconium tert-butoxide, zirconium chloride, zirconium citrate, zirconium ethoxide, zirconium methoxide, zirconium propoxide, and combinations of any two or more thereof.

Suitable molybdenum-containing compounds include, but are not limited to, molybdenum(III) chloride, molybdenum(II) acetate, molybdenum(IV) chloride, molybdenum(V) chloride, molybdenum(VI) fluoride, molybdenum(VI) oxychloride, molybdenum(IV) sulfide, and combinations of two or more thereof.

Examples of suitable germanium-containing compounds include, but are not limited to, germanium chloride, germanium bromide, germanium ethoxide, germanium fluoride, germanium iodide, germanium methoxide, and combinations of any two or more thereof. Examples of suitable indium-containing compounds include, but are not limited to indium acetate, indium bromide, indium chloride, indium fluoride, indium iodide, indium nitrate, indium phosphide, indium selenide, indium sulfate, and combinations of any two or more thereof. Examples of suitable lanthanum-containing compounds include, but are not limited to, lanthanum acetate, lanthanum carbonate, lanthanum octanoate, lanthanum fluoride, lanthanum chloride, lanthanum bromide, lanthanum iodide, lanthanum nitrate, lanthanum perchlorate, lanthanum sulfate, tanthanum titanate, and combinations of any two or more thereof.

Generally, the calcined zeolite-binder can be combined with such coke suppressor precursor in any suitable weight ratios which would result in the weight ratios of a coke suppressor to a zeolite disclosed in the first embodiment of the invention. Presently it is preferred that such combination be carried out in a suitable liquid to form an incipient wetness zeolite-precursor mixture. Upon the calcined zeolite-binder and the precursor are well mixed, the zeolite-precursor mixture is subjected to calcination under substantially the same condition as disclosed above to produce the composition of the first embodiment of the invention.

In the third embodiment of the invention, a process which can be used to convert an olefin to another olefin is provided. The process comprises, consists essentially of, or consists of contacting an olefin with a catalyst composition, optionally in the presence of a hydrogen-containing fluid, under a condition sufficient to convert an olefin to another olefin.

According to the present invention, any olefin, individually or in combination with other olefins, that can be converted by either disproportionation or isomerization to an olefinic compound can be employed. Examples of suitable olefins include, but are not limited to, propylene, n-butenes, n-pentenes, n-hexenes, 4-methyl-1-pentene, and combinations of any two or more thereof. The presently preferred olefins are n-butenes, more preferred olefin is 2-butene, because these butenes can be converted by skeleton isomerization to isobutene which, as disclosed earlier, can be converted to MTBE. Accordingly, isobutene is the presently preferred olefinic compound.

The catalyst composition is the same as the composition disclosed hereinabove in the first embodiment of the present invention.

Any hydrogen-containing fluid which comprises, consists essentially of, or consists of, molecular hydrogen ($H_2$) can be used in the process of this invention. This hydrogen-containing fluid can therefore contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, steam, or combinations of any two or more thereof, or any other fluid which does not significantly affect the process or the catalyst composition used therein.

The contacting of an olefin fluid and a hydrogen-containing fluid in the presence of a catalyst composition can be carried out in any technically suitable manner, in batch, semicontinuous, or continuous process under an effective olefin conversion condition. Generally, a fluid containing an olefin and a hydrogen-containing fluid are separately or simultaneously or combinably introduced into a fixed catalyst bed, or a moving catalyst bed, or a fluidized catalyst bed, or combinations of any two or more thereof by any means known to one skilled in the art such as, for example, pressure, meter pump, and other similar means. The condition can include a weight hourly space velocity (WHSV) of the olefin fluid stream in the range of about 0.01 to about 100, preferably about 0.05 to about 50, and most preferably 0.1 to 30 g feed/g catalyst/hour. The hydrogen-containing fluid hourly space velocity generally is in the range of about 1 to about 10,000, preferably about 5 to about 7,000, and most preferably 10 to 5,000 $ft^3$ $H_2/ft^3$ catalyst/hour. The preferred molar ratio of $H_2$ to the olefin can be in the range of from about 0.01:1 to about 20:1, preferably about 0.1:1 to about 10:1, and most preferably 0.5:1 to 5:1. Generally, the pressure can be in the range of from about 30 to about 1000 psig, preferably about 50 to about 750 psig, and most preferably 200 to 600 psig, and the temperature is about 250° to about 1,000° C., preferably about 450° to about 750° C.

The process effluent generally contains a heavies fraction of compounds having more carbon atoms than the starting olefin to be converted; a lights fraction of molecules having less carbon atoms than the starting olefin to be converted; a non-converted olefin fraction containing the starting olefin; and a desired product olefin fraction. Generally, the effluent can be separated into these principal fractions by, for example, fractional distillation which is well known to one skilled in the art. The non-converted fraction can be recycled to a reactor described above, the lights fraction can be used as fuel gas or as a feed for other reactions. The desired product olefin can be recovered by any means known to one skilled in the art for further use such as, for example, conversion to MTBE.

The following examples are provided to illustrate the present invention and are not to be construed as to limit the scope of the present invention.

EXAMPLE I

This example illustrates the preparation and use of the catalyst of the invention.

A ferrierite (150 g) having the designation of TOSOH HSZ-720KOA (obtained from TOSOH Chemicals, Tokyo, Japan) was blended by mixing, in a beaker, with 4 g of bentonite, 40 g of aluminum chlorohydrate or Chlorohydro® which was 50 weight % aqueous solution obtained from Reheis Inc., Berkeley Heights, N.J. (the aluminum chlorohydrate was mixed with 7.8 g of water), and 124 g of water to form a dough-like mixture. The mixture was then dried in air at 125° C. for 3 hours to produce a dried mixture. The dried mixture was then calcined at 500° C. for 3 hours to produce a an alumina-bound ferrierite (total 129.1 g) which was sized with screens. Of this 129.1 g alumina-bound ferrierite, 19 grams had a particle size between 40–100 mesh (U.S. standard).

The alumina-bound ferrierite having 40–100 mesh size was subsequently suspended with 200 ml of 1.0M ammonium nitrate solution for 64 hours at 70° C. and throughly washed with water followed by drying in air at 120° C. for 3 hours and subsequently calcined at 525° C. (started at 125° C. and ramped at 10° C./min) for 6 hours in a furnace to produce a calcined ferrierite. The calcined ferrierite was analyzed for its silicon and aluminum content. Because zeolites generally also contain a substantially amorphous silica-alumina portion besides the crystalline zeolite portion, total silicon as well as aluminum content was determined by X-ray fluorescence spectrometry employing a Siemens MRS 400 multi-channel spectrometer. This method is well known to one skilled in the art. See, for example, U.S. Pat. Nos. 4,664,025 and 4,975,399, disclosures of which are incorporated herein by reference. The elemental analyses for the alumina-bound ferrierite and calcined ferrierite are shown in Table I below.

TABLE I

| | (Weight %) | | | | | | | |
|---|---|---|---|---|---|---|---|---|
| | Na | Mg | Al | Si | Cl | K | Fe | CA |
| Alumina-bound ferrierite | 0.90 | 0.29 | 5.80 | 28.60 | 0.15 | 3.10 | 0.08 | <0.05 |
| Calcined ferrierite | 0.18 | 0.29 | 6.60 | 30.40 | 0 | 0.27 | 0.08 | 0.12 |

Table I shows that treatment with ammonium nitrate removed most sodium and potassium ions.

The calcined ferrierite (7.5 g) was then blended with 7.0 g of a 50 weight % poly(phenylmethyl) siloxane (PPMS) in cyclohexane (obtained from Dow Chemical, Midland, Mich.). The mixture was calcined at 538° C. in a furnace to produce 8.24 g of silica-incorporated ferrierite. This silicon oxide-incorporated ferrierite containing 10 weight % of silicon oxide by calculation.

In a separate run, a silica-incorporated ferrierite was obtained by using 4.06 g of tetraethyl orthosilicate (TEOS) with 5.0 g of the calcined ferrierite to produce a silicon oxide-incorporated ferrierite containing 5 weight % silicon oxide by calculation.

These silica-incorporated ferrierites were then employed, according to the third embodiment of the invention, in a skeleton isomerization process for converting 2-butene to isobutene. A pure grade 2-butene, obtained from Phillips Petroleum Company, Bartlesville, Okla., was employed as feedstock. The isomerization process was carried out as follows.

A stainless-steel reactor tube (inner diameter 0.75 inch; length: 20 inches) was filled with a 20 ml bottom layer of Alundum® alumina (inert, low surface area alumina), 1.98 g of one of the catalysts in the center position 5 ml, and a 20 ml top layer of Alundum® alumina. Then a liquid 2-butene feed was introduced at a rate of 6 liters/hour (WHSV=7.1), together with hydrogen gas at a rate of 18 liters of $H_2$/hours (molar ratio of $H_2$ to 2-butene=3.23). The retention time was 1.181 seconds, the reaction temperature was 500°–550° C., and the reaction pressure was 18 psig. The reactor effluent was cooled and analyzed with an on-line gas chromatograph at intervals of about 1 hour. The results are shown in Table II.

the unconverted 2-butene was high and can be re-isomerized. More importantly, the by-products (lights and heavies) and coke formation were significantly reduced.

EXAMPLE II

This example illustrates other ferrierite compositions of the invention and processes therewith.

The catalyst compositions were prepared by the same procedure as that disclosed in Example I except that proper amounts of diluted phosphoric acid ($H_3PO_4$) were used in place of a silicon-containing compound to produce phosphorus-containing ferrierites.

In one preparation, 3.0 g of the calcined ferrierite in hydrogen form was mixed with 3.35 g of 10 weight % $H_3PO_4$. The mixture was calcined at 538° C. in air for 6 hours to prepare a phosphorus oxide-incorporated ferrierite having 7.7 weight % (by calculation) or phosphorus oxide. In a separate preparation, 3.0 g of the calcined ferrierite was mixed with 3.24 g of 2.5 weight % $H_3PO_4$ and then calcined at 538° C. for 6 hours to prepare a phosphorus oxide-incorporated ferrierite containing 2.0% phosphorus oxide by calculation. In a further preparation, 7.5 g of the calcined ferrierite was impregnated with 10.01 g of 50 weight %

TABLE II

| Ferrierite incorporated with | $SiO_2$[a] | Reaction Temp (°C.) | Time (hr) | Reactor Effluent (wt %)[b] | | | | |
|---|---|---|---|---|---|---|---|---|
| | | | | lights | isobutene | n-butene | heavies | coke |
| None | 0 | 504 | 1.98 | 21.1 | 13.3 | 21.8 | 52.8 | |
| None | 0 | 504 | 5.55 | 10.8 | 19.6 | 32.6 | 37.0 | 7.4 |
| PPMS | 10 | 500 | 1.20 | 6.4 | 6.1 | 83.0 | 4.5 | |
| PPMS | 10 | 550 | 5.75 | 6.1 | 6.5 | 85.7 | 1.7 | 3.04 |
| TEOS | 5 | 503 | 2.58 | 14.1 | 15.3 | 42.2 | 18.4 | |
| TEOS | 5 | 549 | 4.26 | 11.1 | 19.0 | 59.2 | 10.7 | 3.15 |

[a]The numbers shown are weight % of silicon oxide content, in addition to that originally present in ferrierite, and were determined by weight increase after calcining.
[b]The lights fraction included hydrocarbons containing 1 to 3 carbon atoms; n-butene included 1- and 2-butenes; the heavies fraction include BTX and $C_9$+ aromatic compounds; and coke was determined at the end of a 7-hour run by removing the catalyst from the reactor and determined with a thermal gravimetric analyzer (TGA), manufactured by TA Instruments, New Castle, Delaware.

The results shown in Table II indicate that without PPMS or TEOS treatment, the ferrierite produced very high percentage of lights and heavies which are less valuable than isobutene. Additionally, the coke formation was very high at 7.4%. The PPMS-treated ferrierite produced very low percentage of both lights and heavies. Though isobutene content in the product using PPMS-treated ferrierite was low, $H_3PO_4$ followed by calcination to prepare a phosphorus oxide-incorporated ferrierite having a calculated 32.8 weight % phosphorus oxide.

The process for isomerizing 2-butene was also the same as that disclosed in Example I except the ferrierite catalysts used were those prepared in this example. The results are shown in Table III below.

TABLE III

| Ferrierite incorporated with | wt % Phosphorus Oxide | Reaction Temp (°C.) | Time (hr) | Reaction Effluent (wt %)[a] | | | | |
|---|---|---|---|---|---|---|---|---|
| | | | | lights | isobutene | n-butene | heavies | coke |
| None | 0 | 504 | 5.55 | 10.8 | 19.6 | 32.6 | 37.0 | 7.4 |
| $H_3PO_4$ | 32.8 | 550 | 2.90 | 3.1 | 0.3 | 96.7 | 0 | 0 |
| $H_3PO_4$ | 7.7 | 550 | 5.51 | 4.8 | 1.8 | 93.3 | 0 | 1.2 |
| $H_3PO_4$ | 2.0 | 550 | 5.89 | 7.3 | 30.3 | 61.5 | 1.14 | 1.9 |

[a]See footnote b in Table II.

Table III shows that phosphorus oxide-incorporated ferrierites significantly decreased the lights in the product stream from 10.8% to as low as 0.3% as the phosphorus oxide-incorporated ferrierites also decreased heavies in the product stream from as high as 37.0 weight % to 0. Additionally, the coke formation was reduced from as high as 7.4 weight to 1.9% or less.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed:

1. A process for olefin conversion comprising contacting a first olefin with a catalyst under a condition effective to convert said first olefin to a second olefin wherein said catalyst composition is prepared by a process comprising the steps of:

(1) contacting a zeolite with a binder to produce a zeolite-binder mixture;

(2) calcining said zeolite-binder mixture to produce a calcined zeolite-binder mixture;

(3) impregnating said calcined zeolite-binder mixture with a coke suppressor precursor selected from the group consisting of silicon-containing compounds and phosphorus-containing compounds and combinations thereof under a condition sufficient to incorporate the coke suppressor onto the zeolite to form a modified zeolite; and (4) calcining the modified zeolite under a condition sufficient to convert the coke suppressor precursor to its oxide form wherein the amount of the coke suppressor precursor is the amount that is sufficient to produce a coke-suppressing amount of said coke suppressor.

2. A process according to claim 1 wherein said coke suppressor precursor is selected from the group consisting of a silicon-containing compound having a formula of (R)(R)(R)Si—(O$_m$Si(R)(R)—)$_n$R wherein each R is independently selected from the group consisting of alkyl radicals, alkenyl radicals, aryl radicals, alkaryl radicals, aralkyl radicals, and combinations of any two or more thereof; m is 0 or 1; and n is 1 to about 10 wherein each radical contains 1 to about 15 carbon atoms.

3. A process according to claim 1 wherein said coke suppressor precursor is selected from the group consisting of poly(phenylmethylsiloxane), poly(phenylethylsiloxane), poly(phenylpropylsiloxane), hexamethyldisiloxane, decamethyltetrasiloxane, diphenyltetramethyldisiloxane, tetraethyl orthosilicate, trimethylchlorosilane, chloromethyldimethylchlorosilane, N-trimethylsilylimidazole, N,O-bis(trimethylsilyl)acetimide, N-methyl-N-trimethylsilyltrifuoroacetamide, t-butyldimethylsilylimidazole, N-trimethylsilylacetamide, methyltrimethoxysilane, vinyltriethoxysilane, ethyltrimethoxysilane, propyltrimethoxysilane, (3,3,3-trifluoropropyl)trimethoxysilane, [3-(2-aminoethyl)aminopropyl]trimethoxysilane, cyanoethyltrimethoxysilane, aminopropyltriethoxysilane, phenyltrimethoxysilane, (3-chloropropyl)trimethoxysilane, (3-mercaptopropyl)trimethoxysilane, (3-glycidoxypropyl)trimethoxysilane, vinyltris(β-methoxyethoxy)silane, (γ-methacryloxypropyl)trimethoxysilane, vinylbenzyl cationic silane, (4-aminopropyl)triethoxysilane, [γ-(β-aminoethylamino)propyl]trimethoxysilane, (γ-glycidoxypropyl)trimethoxysilane, [β-(3,4-epoxycyclohexyl)ethyl]trimethoxysilane, (β-mercaptoethyl)trimethoxysilane, (γ-chloropropyl)trimethoxysilane, and combinations of any two or more thereof.

4. A process according to claim 1 wherein said coke suppressor precursor is selected from the group consisting of phosphorus pentoxide, phosphorus oxychloride, P(OR)$_3$, P(O)(OR)$_3$, P(O)(R)(R)(R), P(R)(R)(R), and combinations of any two or more thereof wherein each R is independently selected from the group consisting of hydrogen, alkyl radicals, alkenyl radicals, aryl radicals, alkaryl radicals, aralkyl radicals, and combinations of any two or more thereof; each radical contains 1 to about 15 carbon atoms.

5. A process according to claim 1 wherein said coke suppressor precursor is poly(phenylmethylsiloxane).

6. A process according to claim 1 wherein said coke suppressor precursor is tetraethyl orthosilicate.

7. A process according to claim 1 wherein said first olefin is selected from propylene, n-butenes, n-pentenes, n-hexenes, 4-methyl-1-pentene, and combinations of any two or more thereof.

8. A process according to claim 1 wherein said first olefin is 2-butene.

9. A process for olefin conversion comprising contacting a first olefin with a catalyst composition under a condition effective to convert said first olefin to a second olefin wherein;

said catalyst comprises a zeolite having incorporated therein a coke suppressor selected from the group consisting of silicon oxides and phosphorous oxides and combinations thereof;

the weight ratio of said coke suppressor to said zeolite is in the range of from about 0.0001:1 to about 1:1;

said catalyst composition is prepared by a process comprising the steps of: (1) contacting a zeolite with a binder to produce a zeolite-binder mixture; (2) calcining said zeolite binder mixture to produce a calcined zeolite-binder mixture; (3) impregnating said calcined zeolite binder mixture with a coke suppressor precursor selected from the group consisting of silicon containing compounds and phosphorous containing compounds and combinations thereof under a condition sufficient to incorporate the coke suppressor onto the zeolite to form a modified zeolite; and (4) calcining the modified zeolite under a condition sufficient to convert the coke suppressor precursor to its oxide form;

said silicon containing compound comprising a formula of (R)(R)(R) Si—(—O$_m$Si(R)(R)—)$_n$R;

said phosphorous-containing compound is selected from the group consisting of phosphorous pentoxide, phosphorous oxychloride, P(OR)$_3$, P(O)(OR)$_3$, P(O)(R)(R)(R), P(R)(R)(R), and combinations of any of two or more thereof and wherein each R is independently selected from the group consisting of hydrogen, alkyl radicals, alkenyl radicals, aryl radicals, alkaryl radicals, aralkyl radicals, and combinations of any of two or more thereof; m is 0 or 1; and n is 1 to about 10 wherein each radical contains 1 to about 15 carbon atoms.

10. A process according to claim 9 wherein said silicon-containing compound is selected from the group consisting of poly(phenylmethylsiloxane), poly(phenylethylsiloxane), poly(phenylpropylsiloxane), hexamethyldisiloxane, decamethyltetrasiloxane, diphenyltetramethyldisiloxane, tetraethyl orthosilicate, trimethylchlorosilane, chloromethyldimethylchlorosilane, N-trimethylsilylimidazole, N,O-bis(trimethylsilyl) acetimide, N-methyl-N-trimethylsilyltrifluoroacetamie, t-butyldimethylsilylimidazole, N-trimethylsilylacetamide, methyltrimethoxysilane, vinyltriethoxysilane, ethyltrimethoxysilane, propyltrimethoxysilane, (3,3,3-trifluoropropyl)trimethoxysilane, [3-(2-aminoethyl) aminopropyl]trimethoxysilane, cyanoethyltrimethoxysilane, aminopropyltriethoxysilane, phenyltrimethoxysilane, (3-chloropropyl)trimethoxysilane, (3-mercaptopropyl) trimethoxysilane, (3-glycidoxypropyl)trimethoxysilane, vinyltris(β-methoxyethoxy)silane, (γ-methacryloxypropyl) trimethoxysilane, vinylbenzyl cationic silane, (4-aminopropyl)triethoxysilane, [γ-(β-aminoethylamino) propyl ]trimethoxysilane, (γ-glycidoxypropyl) trimethoxysilane, [β-(3,4-epoxycyclohexyl)ethyl] trimethoxysilane, (β-mercaptoethyl)trimethoxysilane, (γ-chloropropyl)trimethoxysilane, and combinations of any two or more thereof.

11. A process according to claim 9 wherein said coke suppressor precursor is poly(phenylmethylsiloxane).

12. A process according to claim 9 wherein said coke suppressor precursor is tetraethyl orthosilicate.

13. A process according to claim 9 wherein said first olefin is selected from propylene, n-butenes, n-pentenes, n-hexenes, 4-methyl- 1-pentene, and combinations of any two or more thereof.

14. A process according to claim 9 wherein said first olefin is 2-butene.

15. A process according to claim 1 wherein said catalyst consists essentially of a ferrierite and a coke-suppressing amount of a coke suppressor selected from the group consisting of silicon oxides and phosphorus oxides and combinations thereof.

16. A process according to claim 9 wherein said catalyst consists essentially of a ferrierite and a coke-suppressing amount of a coke suppressor selected from the group consisting of silicon oxides and phosphorus oxides and combinations thereof.

* * * * *

UNITED STATES PATENT AND TRADEMARK OFFICE
CERTIFICATE OF CORRECTION

PATENT NO. : 5,877,379

DATED : March 2, 1999

INVENTOR(S) : An-hsiang Wu and Charles A. Drake

It is certified that error appears in the above-identified patent and that said Letters Patent is hereby corrected as shown below:

On title page, item [75], inventor Charles A. Drake is from Nowata, Okla.

Column 11, claim 2, line 41, delete "$(R)(R)(R)Si\text{-}(\text{-}O_mSi(R)(R)\ )R$" and insert ---$(R)(R)(R)Si\text{-}(\text{-}O_mSi(R)(R)\ )_nR$---.

Column 12, claim 9, line 49, delete "$(R)(R)(R)Si\text{---}(\text{---}O_mSi(R)(R)\text{---})_nR$" and insert ---$(R)(R)(R)Si\text{---}(\text{---}O_mSi(R)(R)\text{---})_nR$---.

Signed and Sealed this

Seventh Day of September, 1999

Attest:

Q. TODD DICKINSON

*Attesting Officer*     *Acting Commissioner of Patents and Trademarks*